(12) United States Patent
Segeral

(10) Patent No.: US 6,182,505 B1
(45) Date of Patent: Feb. 6, 2001

(54) METHOD AND APPARATUS FOR STUDYING THE PROPERTIES OF A MULTIPHASE FLUID UNDER PRESSURE FLOWING IN A DUCT, SUCH AS A PETROLEUM STREAM

(75) Inventor: Gerard Segeral, Gif sur Yvette (FR)

(73) Assignee: Schlumberger Technology Corporation, Ridgefield, CT (US)

( * ) Notice: Under 35 U.S.C. 154(b), the term of this patent shall be extended for 0 days.

(21) Appl. No.: 08/971,819

(22) Filed: Nov. 17, 1997

(30) Foreign Application Priority Data

Nov. 22, 1996 (FR) .................................................. 96 14292

(51) Int. Cl.$^7$ ............................ G01F 5/00; G01N 33/28; G01N 27/22; E21B 49/08
(52) U.S. Cl. ................... 73/61.44; 73/861.04; 73/64.56; 73/152.42; 422/68.1; 95/259
(58) Field of Search ................................ 73/61.44, 64.56, 73/64.44, 61.41, 61.43, 861.04, 152.42, 152.18; 95/259; 422/68.1

(56) References Cited

U.S. PATENT DOCUMENTS

| | | | |
|---|---|---|---|
| 2,225,798 | 12/1940 | Price .......................................... 73/21 |
| 4,144,754 | 3/1979 | Pitts, Jr. et al. ......................... 73/205 |
| 4,147,062 | * 4/1979 | Jaeger ............................... 73/422 GC |
| 4,167,117 | 9/1979 | Stokley et al. ....................... 73/422 R |
| 4,215,567 | 8/1980 | Vicek ................................. 73/61.1 R |
| 4,262,533 | * 4/1981 | Jaeger ............................... 73/422 TC |
| 4,494,413 | 1/1985 | Bukkems et al. .................. 73/863.43 |
| 4,656,869 | * 4/1987 | Zacharias ................................. 73/597 |
| 4,776,210 | * 10/1988 | Baillie et al. ...................... 73/61.1 R |
| 4,813,270 | 3/1989 | Baillie .................................. 73/61 R |
| 5,033,288 | * 7/1991 | Castel ................................ 73/61.1 R |
| 5,055,202 | * 10/1991 | Carroll et al. .......................... 210/739 |
| 5,070,725 | * 12/1991 | Cox et al. .......................... 73/61.1 R |
| 5,101,164 | * 3/1992 | Marrelli ................................ 324/640 |
| 5,103,181 | * 4/1992 | Gaisford et al. ....................... 324/637 |
| 5,127,272 | * 7/1992 | Dean et al. ......................... 73/861.04 |
| 5,211,842 | * 5/1993 | Tuss et al. .............................. 210/87 |
| 5,394,339 | * 2/1995 | Jones ..................................... 364/510 |
| 5,415,024 | * 5/1995 | Proffitt et al. ........................ 73/61.44 |
| 5,417,107 | * 5/1995 | Biencourt et al. ................... 73/61.44 |
| 5,591,922 | 1/1997 | Segeral et al. ..................... 73/861.04 |
| 5,597,961 | * 1/1997 | Marelli .............................. 73/861.04 |
| 5,660,617 | * 8/1997 | Hatton .................................... 95/254 |
| 5,673,026 | * 9/1997 | Marrelli et al. ....................... 340/608 |
| 5,747,674 | * 5/1998 | Moracchini et al. ............... 73/61.44 |

FOREIGN PATENT DOCUMENTS 2 254 234    7/1975   (FR) ................................ F04F/3/00

OTHER PUBLICATIONS

Alderson, A. and Demulder, B. Homogeneisation d'un fluide par utilisation d'une boucle verticale. *Petrole et Techniques,* Paris France. No. 296 (Mar. 1983) pp. 68–78, XP002036741. Photos OK.

* cited by examiner

Primary Examiner—Hezron Williams
Assistant Examiner—J. David Wiggins
(74) Attorney, Agent, or Firm—William B. Batzer

(57) ABSTRACT

To study the properties of a multiphase fluid under pressure flowing along a duct, such as the petroleum stream produced by an oil well, a fraction of the fluid is taken from a substantially vertical first length of the duct within which the fluid is agitated and flows upwards, and this fraction is transferred into a separator receptacle with the top of said receptacle being connected to a second length of the duct located downstream from the first length and at a slightly lower pressure relative thereto. Thereafter, the volume ratio of the liquid phases can be determined, e.g. by pouring them into the separator receptacle and measuring the levels thereof, or by causing the liquid emulsion to flow through an appropriate sensor device and where the emulsion density can be determined by weighing the separator receptacle before and after such a liquid phase/emulsion pouring step.

17 Claims, 2 Drawing Sheets

METHOD AND APPARATUS FOR STUDYING THE PROPERTIES OF A MULTIPHASE FLUID UNDER PRESSURE FLOWING IN A DUCT, SUCH AS A PETROLEUM STREAM

BACKGROUND OF THE INVENTION

Technical Field

The invention relates to a method and to apparatus for studying the properties of a multiphase fluid under pressure flowing along a duct and containing at least two liquid phases and one gaseous phase. The method and the apparatus of the invention make it possible, in particular, to determine the volume ratio of the liquid phases and to perform other measurements, such as density measurements, on each of the liquid phases.

A particular application of the invention lies in studying the properties of a petroleum stream flowing along a surface duct connected to one or more oil wells.

Background Information

Exact knowledge of the volume or mass ratios of the various fluid phases taken from an oil well is essential for operating the well.

In practice, such knowledge is difficult to acquire because oil well effluents generally comprise two liquid phases, constituted by water and liquid petroleum, plus a gas phase constituted by gaseous hydrocarbons, frequently in association with a solid phase constituted by sediment, sand, etc.

The volume or mass ratios of the various phases are frequently determined from a sample taken from the multiphase fluid under pressure flowing in the duct concerned. The most accurate technique for performing such sample-taking consists in enclosing a flowing fluid sample between two quick-closing valves placed directly in the duct or in a duct connected in parallel therewith. That technique has the advantage of enabling global measurement to be performed over the entire section of the duct concerned. However it depends on the speed with which the valves can close, and the number of valves concerned must be doubled when a parallel duct is provided, which is essential if it is desired that the flow of fluid should continue while a sample is being taken.

Such valve closure speed requires high control power and gives rise to high cost. In addition, the use of valves having moving parts constitutes a clear handicap from the point of view of reliability. Finally, it should be observed that this technique is unsuitable for performing accurate analysis of the fluid when the gaseous phase predominates to a large extent (e.g. constituting greater than 90% by volume). The quantity of liquid taken is then insufficient to enable accurate measurements to be performed. For all these reasons, the above technique is not used.

Given the difficulties raised by the technique of using quick-closing valves a simpler technique has been developed for the purpose of taking a plurality of small-volume samples in succession and accumulating the liquid phases of said successive samples in a common tank. That technique is illustrated in particular by U.S. Pat. Nos. 4,147,062 and 4,262,533, and it makes it possible to determine over a certain period, the mean volume ratio of the liquid phases contained in the fluid under pressure flowing along the duct. The samples are taken by means of a piston driven with reciprocating motion in a cylinder that opens out radially into the duct concerned. The two ends of the piston are in sealing relationship with the cylinder while the central portion of the piston has an annular recess. In the advanced position of the piston, its annular recess is located in the duct and is filled with fluid. When the piston is retracted into the cylinder, a small quantity of fluid is captured in the annular recess of the piston. The liquid phases of the fluid then fall under gravity into a tank while the gaseous phase is conventionally returned to the duct.

Although that piston sample-taking technique is simpler to implement than the quick-closing valve technique, it too suffers from the drawback of requiring the presence of moving parts that can give rise to breakdown. U.S. Pat. No. 4,776,210 proposes another sample-taking technique. In that case, the duct along which the multiphase fluid under pressure flows includes a horizontal portion in which fluid flow is reversed. More precisely, the fluid arrives in a given direction via a first horizontal duct that opens out facing a vertical wall. After striking the wall, the fluid rebounds in the opposite direction into a second horizontal duct disposed either around the first or to one side of it.

In accordance with U.S. Pat. No. 4,776,210, a small fraction of fluid is taken via at least one tube opening out in line with the end of the first duct. The other end of the tube is connected to a centrifugal separator whose top communicates via a second tube with a length of the duct situated downstream from the fluid flow reversal system, to return the gas phase thereto. The liquid phases collected in the bottom of the centrifugal separator are returned to the duct but significantly further downstream, after passing through an electromagnetic radiation measuring apparatus for determining the fraction of water present in the liquid phases.

Although the technique described in U.S. Pat. No. 4,776,210 makes it possible to eliminate moving parts, it suffers from the significant drawback of greatly disturbing the flow of fluid and of requiring significant modification to the length of duct from which the sample is taken.

It should also be noted that the accuracy with which the properties of a multiphase fluid are studied, e.g. the volume ratio of the liquid phases it contains, depends on the representativeness of the sample taken. The representativeness of the sample taken depends in particular on preserving thermodynamic equilibrium, i.e. on maintaining pressure and temperature during sample-taking and throughout subsequent operations. Unfortunately, maintaining thermodynamic equilibrium, and in particular temperature, is not described in the prior art.

SUMMARY OF THE INVENTION

A main object of the invention is to provide a method enabling the properties of a multiphase fluid under pressure and flowing along a duct to be studied, e.g. the volume ratio of its liquid phases, without requiring moving parts or other complex mechanisms that are expensive and unreliable, and without requiring significant modification to the duct or to fluid flow within the duct. According to the invention, this result is obtained by means of a method of studying the properties of a multiphase fluid flowing along a duct and containing at least two liquid phases and a gaseous phase, which comprises the following steps: a fraction of fluid is extracted from a substantially vertical first length of the duct, within which the fluid is agitated and flows upwards, the fraction being taken at a certain distance from the wall of said length; and the taken fluid fraction is transferred into a separator receptacle whose top portion is connected to the second length of the duct located downstream from the first length and within which the pressure is slightly lower than that of the first length so that a fluid sample is obtained which conserves the volume ratio of the liquid phases.

In order to preserve thermodynamic equilibrium, a thermally-insulated separator receptacle is used within which there obtains initially a pressure that is close to that which obtains in the first length.

To guarantee that the volume ratio between the liquid phases within the sample take is preserved, all liquid is initially eliminated from the separator receptacle by filling said receptacle and the tubes which connect it to the duct with a gas at a pressure close to that which obtains in the first length. In a first application of the method of the invention, the volume ratio of the liquid phases is then determined.

To this end, it is possible to isolate the separating receptacle from the duct and to measure the levels of the liquid-gas and liquid-liquid interfaces in the receptacle. This constitutes a measurement that is performed discontinuously at specific instants.

In this first application of the method of the invention, it is thus possible to determine the volume ratio of the liquid phases by connecting the bottom of the separator receptacle continuously to the second length of the duct, via apparatus for measuring said ratio.

In another application of the method of the invention, the density of an emulsion of the liquid phases is subsequently determined by isolating the separator receptacle from the duct, by weighing the separator receptacle before and after sample-taking, and by measuring the level of the liquid-gas interface in the receptacle.

In yet another application of the method, the separator receptacle is subsequently isolated from the duct, after which each of the liquid phases is drawn off successively therefrom in order to study its properties separately.

To implement the method of the invention, it is preferable to use a separator receptacle that is cylindrical, having a vertical axis, and an inside cross section that is substantially uniform.

The fluid in the first length from within which the sample is taken can be agitated in various different ways. In a preferred embodiment, the first length is situated immediately above a first Venturi that provides agitation. In this way, samples can be taken, for example, immediately after a Venturi belonging to a flow measuring system.

Also, in order to transfer the fluid sample taken into the separator receptacle, it is advantageous to connect the top of the receptacle to a second Venturi belonging to a flow measuring system and forming a second length of duct. There again, that configuration constitutes only a preferred embodiment, and other means can be used to establish a small amount of suction in the second length of the duct relative to the first length. Amongst such other means, mention may be made by way of example of the presence of a valve establishing a head loss immediately upstream from the second length into which the gaseous phase is exhausted. In a preferred use of the method of the invention, the fluid is an oil well effluent, containing water and liquid and gaseous hydrocarbons. The invention also provides apparatus for studying the properties of a multiphase fluid flowing along a duct and containing at least two liquid phases and a gaseous phase, the apparatus comprising: a sample-taking tube having a first end opening out into a substantially vertical first length of the duct within which the fluid is agitated and flows upwards, and which opens out within said length at a certain distance from the wall thereof; a separator receptacle into which there opens out a second end of the sample-taking tube; a tube for exhausting the gaseous phase, said tube connecting the separator receptacle to a second length of the duct, placed downstream from the first length, and at a slightly lower pressure than said first length; and valve-forming means placed in the sample-taking tube and in the tube for exhausting the gaseous phase.

In order to preserve thermodynamic equilibrium, the separator receptacle includes thermal insulation. In an embodiment of the apparatus of the invention, the apparatus includes means for measuring the levels of the liquid-gas and the liquid-liquid interfaces in the separator receptacle. These level-measuring means make it possible to determine the volume ratio of the liquid phases.

In this embodiment, apparatus for measuring the volume ratio of the liquid phases can also be placed in a tube for discharging the liquid phases, connecting the bottom of the separator receptacle to the second length of the duct. The separator receptacle preferably includes transparent vertical tubes surrounded by a metal outer sheath, with an observation window being formed through the sheath.

BRIEF DESCRIPTION OF THE DRAWINGS

Two preferred embodiments of the invention are described below as non-limiting examples with reference to the accompanying drawings, in which.

DETAILED DESCRIPTION OF PREFERRED EMBODIMENTS

Figure 1:
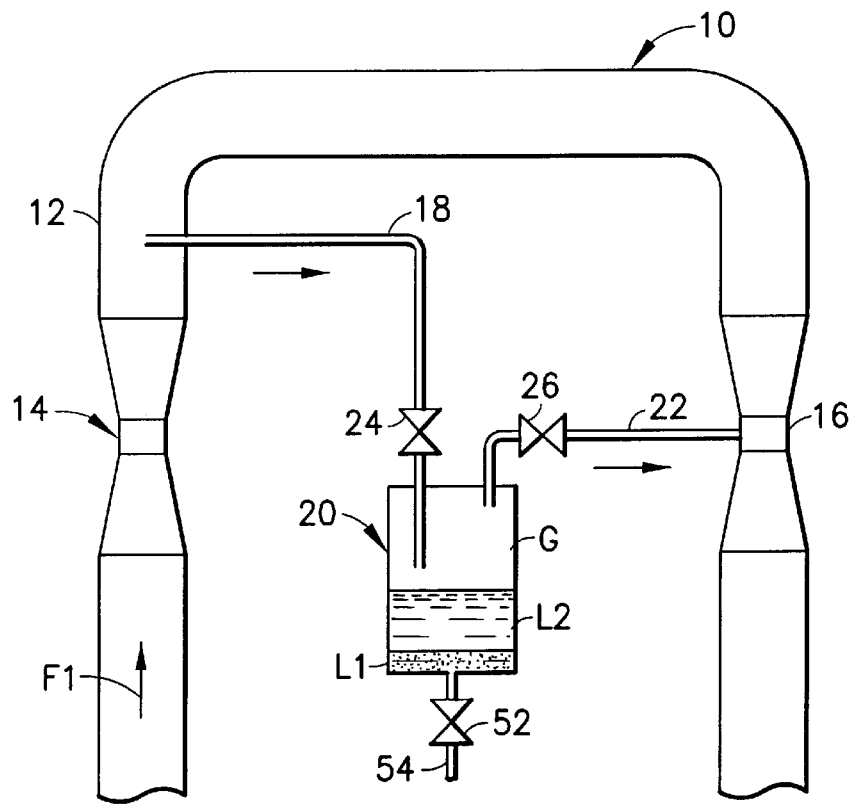
FIG. 1 is a diagram of apparatus constituting a first embodiment of the invention, in which the volume ratio of the liquid phases in a multiphase fluid under pressure flowing along a duct is determined in discontinuous manner.

In FIG. 1, reference 10 designates in general a duct within which there flows a multiphase fluid under pressure, which fluid contains at least two liquid phases and one gaseous phase.

Although the fluid flowing in the duct 10 may be of various different kinds, the invention is advantageously applicable to oil well effluents in which the liquid phases are constituted by water and by liquid petroleum while the gaseous phase is constituted by gaseous hydrocarbons. The duct 10 is then a surface duct in which the effluents from one or more oil wells are caused to flow. In this particular application, it should be observed that the fluid frequently contains a fourth phase constituted by solids in divided form, such as sediments, sand, etc.

In order to accommodate the apparatus of the invention, the duct 10 includes a first length 12 that extends substantially vertically and along which the fluid flows upwards, as represented by arrow F 1. Also, the fluid reaching said first length 12 is sufficiently agitated to ensure that the various phases constituting it are distributed therein as uniformly as possible. Such agitation of the fluid in the length 12 can be obtained by various different means, for example a perforated tube or plate located immediately upstream from the first length 12, i.e. immediately beneath it.

In the preferred embodiment shown in FIG. 1, the fluid in the first length 12 is agitated by means of a first Venturi 14 placed in the duct 10 immediately upstream from the length 12, i.e. immediately beneath said length. This embodiment presents the advantage of enabling the apparatus of the invention to be installed with practically no modification to the duct 10.

As shown in particular in European patent application 0 684 458 (equivalent to U.S. Pat. No. 5,591,922), incorporated herein by reference, various Venturis are often placed in ducts conveying a petroleum fluid on the surface, in order to perform various measurements of the fluid, such as flow rate measurements. Thus, document EPA-0 684 458 describes a flow meter system in which two Venturis are spaced apart by a given distance along a common duct within which there flows a multiphase fluid. By measuring the pressure drop induced by each of the Venturis, it is possible by a correlation-method to determine the time lapse required for the multiphase fluid to travel the distance between the two Venturis. Document EP-A-0 684 458 also envisages adding to the system means for measuring the density of the fluid, which means comprise a member for measuring the pressure difference between two different levels of a common vertical duct.

To enable apparatus of the invention to be installed, the duct 10 also includes, downstream from the first length 12, a second length 16 within which the pressure is, temporarily or permanently, slightly less than that prevailing in length 12. This second length 16 is situated downstream from the first length 12. It can extend in any direction.

A pressure that is slightly less than that prevailing in the first length 12 can be established temporarily or permanently in the second length 16 by any appropriate means. Such means include, for example, the presence of a perforated plate or of a valve immediately upstream from the second length 16 of the duct 10. When a valve is used, it is normally open and it is closed partially whenever the apparatus of the invention is put into operation, thereby avoiding disturbance to the fluid flow outside periods during which the apparatus is put into operation.

In the embodiment shown in FIG. 1, pressure is established in the second length 16 of the duct 10 slightly below the pressure prevailing upstream in the first length 12 by implementing said second length 16 in the form of a second Venturi likewise forming part of a flow rate measuring system of the kind described in document EP-A-0 684 458.

In the first embodiment of the invention, as shown in FIG. 1, the apparatus for measuring the volume ratio of the liquid phases in the fluid traveling along the duct 10 essentially comprises a sample-taking tube 18, a separating receptacle 20, and a tube 22 into which the gaseous phase is exhausted. These elements are associated with first valve-forming means 24 placed in the sample-taking tube 18, second valve-forming means 26 placed in the sample-taking tube 22, and third valve-forming means 52 placed in a liquid phase exhaust tube 54 opening out into the end wall of the separating receptacle 20.

The sample-taking tube 18 connects the first length 12 of the duct 10 to the separating receptacle 20. More precisely, the first end of the sample-taking tube 18 opens out into the first length 12, at a certain distance from the wall thereof. This arrangement makes it possible to ensure that the sample of fluid is indeed taken from a zone containing a homogeneous mixture of the various fluid phases, which would not be the case if sample-taking were performed along the wall.

The first end of the sample-taking tube 18 through which the fluid sample is taken can have various different shapes. In the simplest shape shown in FIG. 1, the tube 18 opens out radially into the inside of the duct 10 via an orifice situated in a plane parallel to the axis thereof, i.e. in a substantially vertical plane given that the axis of the first length 12 is itself substantially vertical. This embodiment is advantageous both for its simplicity and because it makes it possible to avoid taking solid particles that might possibly be conveyed by the fluid. In a variant, the first end of the sample-taking tube 18 may nevertheless be different in shape, for example it may be curved downwards, it may be in the form of a perforated tube, etc.

Figure 2:
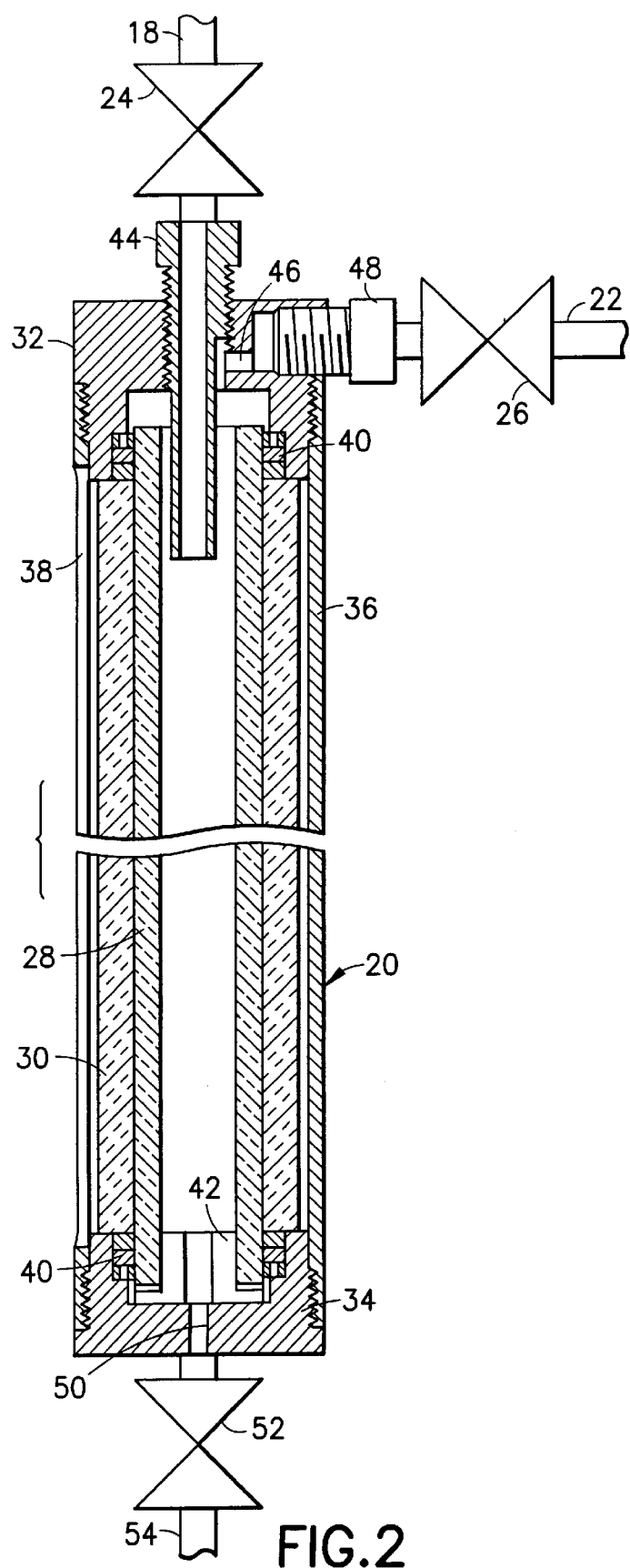
FIG. 2 is a vertical section view showing in greater detail a separator receptacle used in the apparatus of FIG. 1.

The first valve-forming means 24 is situated in the sample-taking tube 18 close to the separator receptacle 20, and the second end of the sample-taking tube 18 opens out into said receptacle, preferably in the top portion thereof as shown more clearly in FIG. 2.

The gas phase exhaust tube 22 connects the separator receptacle 20 to the second length 16 of the duct 10. More precisely, a first end of the tube 22 opens out into the top of the separator receptacle 20, preferably at a level that is higher than the level of the second end of the sample-taking tube 10. The second end of the gas phase exhaust tube 22 is connected to the second length 16 of the duct 10, i.e. directly to the second Venturi in the preferred first embodiment of FIG. 1. The second valve-forming means 26 is preferably placed close to the separator receptacle 20.

As shown in greater detail in FIG. 2, the separator receptacle 20 is preferably a cylindrical receptacle, having a vertical axis and an inside section that is substantially uniform over its entire height.

More precisely, the separator receptacle 20 comprises a transparent vertical tube 28, e.g. made of glass, with the inside volume thereof constituting the working volume of the receptacle. Over the major portion of its height, and with the exception of its ends, the transparent vertical tube 28 is surrounded by a thermally insulating sheath 30 of plastics material that is likewise transparent, and that is hot-shrunk onto the tube 28. The thermally insulating sheath 30 has a major function of keeping the fluid sample at approximately the same temperature as that which obtains in the duct. It also has the function of making it easier for the tube 28 to withstand the pressure of the fluid received in the separator receptacle 20.

The thermally insulating sheath 30 is placed between a top endpiece 32 and a bottom endpiece 34 which close the ends of the separator receptacle 20. The endpieces 32 and 34 are metal pieces that are connected together by a metal sheath 36 disposed coaxially around the tube 28 and the thermally insulating sheath 30, and whose ends are screwed onto the endpieces.

In the embodiment shown in FIG. 2, the volume ratio of the liquid phases admitted into the separator receptacle 20 can be determined by visually measuring the levels of the liquid-gas interface and of the liquid-liquid interface in the separator receptacle 20. To enable such visual measurement to be performed, the tube 28 and the thermally insulating sheath 30 of plastics material are transparent. In addition, a window 38 is formed through the metal outer sheath 36, parallel to the vertical axis of the receptacle and extending over the entire height of said sheath between the endpieces 32 and 34.

It should be observed that in a variant, the levels of the liquid-gas interface and of the liquid-liquid interface within the separator receptacle 20 need not be measured visually, but can be measured by means of level-measuring devices operating using known techniques, e.g. optical means. Under such circumstances, the separator receptacle may be implemented in some other material. In particular, the presence of transparent parts and of an observation window is no longer necessary.

In order to guarantee that the volume defined inside the tube 28 is sealed from the outside, in spite of the presence of the observation window 38, while still allowing differential expansion to take place between the glass tube 28 and the metal outer envelope of the receptacle as constituted by the endpieces 32 and 34 and by the metal outer sheath 36, annular metal sealing members 40 are interposed between each of the endpieces 32 and 34 and the corresponding ends of the tube 28.

Also, a tubular endpiece 42 is engaged in the bottom end of the tube 28 received in the bottom endpiece 34 in order to reduce as much as possible the dead volumes within the bottom portion of the separator receptacle 20 for receiving the liquid phases of the fluid. In the embodiment shown in FIG. 2, the sample-taking tube 18 passes through the top endpiece 32 along a vertical axis that is close to the axis of the separator receptacle, so as to have a second end that opens out into the top portion of the glass tube 28. Specifically, said second end of the tube 18 is formed in a coupling 44 which is screwed into the top endpiece 32 and which carries the first above valve-forming means 24 of said endpiece.

The first end of the gas phase exhaust tube 22 is connected directly to the endpiece 32 so as to open out into the top of the separator receptacle 20 via a passage 47 machined in said endpiece. More precisely, the first end of the tube 22 is implemented in the form an endpiece 48 that is screwed in a threaded portion of the passage 46 that extends radially outwards. This endpiece 48 carries the second valve-forming means 26.

As shown in FIG. 2, the bottom endpiece 34 has a passage 50 passing axially therethrough and controlled by the third valve-forming means 52. This organization makes it possible to exhaust the liquid phases contained in the separator receptacle 20 after the levels of the interfaces have been measured within the receptacle. As explained below, this also makes it possible to use the same separator receptacle 20 in the second preferred embodiment of the invention.

When implementing the apparatus described above with reference to FIGS. 1 and 2, in order to obtain a sample that is representative of the liquid phases contained in the fluid, it is necessary to empty the liquid completely from the apparatus before taking any sample. Also, preserving thermodynamic equilibrium means that it is necessary to establish an initial pressure in the apparatus that is close to the pressure that obtains in the duct.

Those two conditions are achieved simultaneously by ensuring that the apparatus is filled and pressurized, i.e. the separator receptacle 20 and the tubes 18 and 22 are filled and pressurized, by means of a gas at a pressure that is close to that which obtains in the first length 12 of the duct 10. The gas under pressure injected into the apparatus can either be a gas taken from a cylinder containing gas at an appropriate pressure, or else it can be gas extracted from the fluid flowing along the duct, at some other point thereof. In order to guarantee that all of the liquid is exhausted, the operation is repeated several times.

Once the apparatus has been filled and pressurized, the valve-forming means 24 and 26 are opened while the valve-forming means 52 remain closed. A sample of the fluid is taken automatically from the first length 12 via the sample-taking tube 18 under the effect of the pressure difference that exists between the first length 12 and the second length 16 to which the tube 22 is connected. While the sample is being taken, the liquid phases are trapped in the bottom of the separator receptacle 20, while the gaseous phase is conveyed automatically into the duct 10 via the tube 22. The level of the liquid phases thus increases progressively, within the separator receptacle 20.

Sample-taking is stopped by simultaneously controlling the valve-forming means 24 and 26 while the level of the liquid phases in the top receptacle 20 is high enough to make it possible to perform a measurement on a volume of liquid that is sufficient while remaining less than a level above which liquid phase overflow via the tube 22 might take place. In the previously described embodiment, said level is detected visually through the observation window 38 because the thermal projection sheath 30 and the tube 28 are transparent.

By injecting into the separator receptacle 20 a de-emulsifying substance, for accelerating separation between the liquid phases, and/or by allowing the liquid phases to rest for a sufficient length in time to enable phase separation to take place, it is possible to find in the separator receptacle 20, starting from the bottom: a first liquid phase L1, e.g. constituted by water; a second liquid phase L2, e.g. constituted by liquid petroleum; and a gaseous phase G, e.g. constituted by gaseous hydrocarbons.

The levels of the liquid-liquid interface between the liquid phases L1 and L2 and of the liquid-gas interface between the liquid phase L2 and the gas phase G are then measured. This measurement can be performed visually as is made possible by the above-described embodiment, or by means of any level detector apparatus suitable for being implanted in the separator receptacle 20.

The volume ratio of the liquid phases L1 and L2 can be deduced from such measurements merely by determining the ratio of the depths of each of the liquids L1 and L2 within the separator receptacle 20.

It should be observed that the apparatus of the invention makes it possible to acquire certain other kinds of information such as the density of an emulsion formed by two liquids L1 and L2. Ignoring the mass of the gaseous phase G, weighing the separator receptacle 20 before and after sample-taking serves to obtain the mass of the liquid emulsion and the density of said emulsion can be deduced therefrom, given the measured total depth of the liquid phases L1 and L2 in the receptacle. Where necessary, a correction can be performed when the density of the gas phase is known.

It is also possible to withdraw the liquid phase L1 and then the liquid phase L2 in succession through the passage 50. Other characteristics of said liquid phases can be deduced by performing measurements on each of the samples withdrawn in this way.

Figure 3:
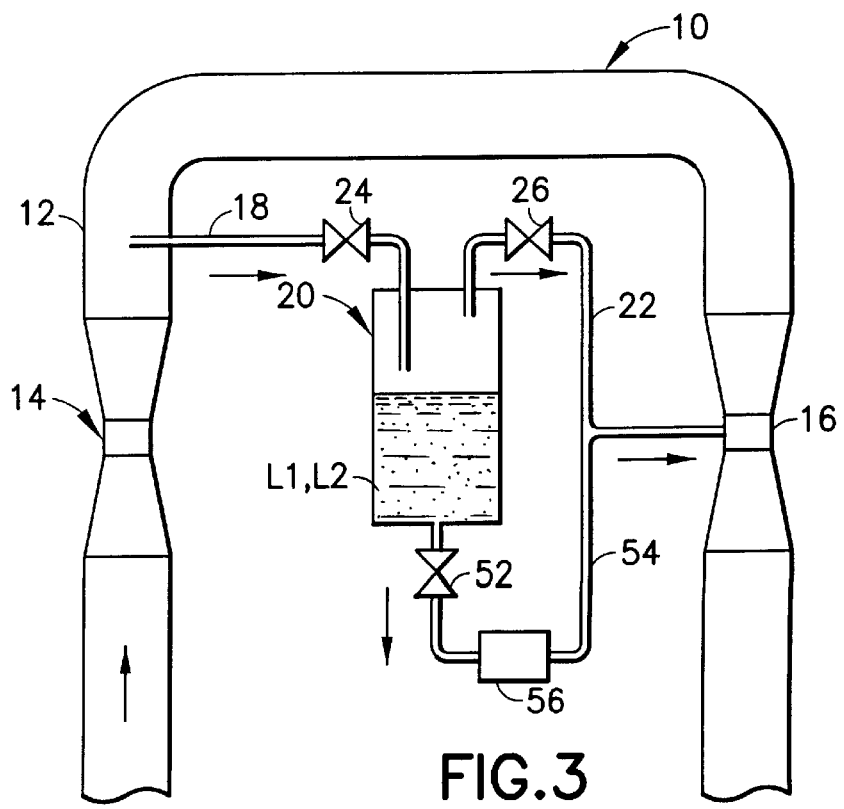
FIG. 3 is a diagrammatic view similar to FIG. 2, showing apparatus constituting a second embodiment of the invention and enabling the volume ratio of the liquid phases in a multiphase fluid under pressure flowing along a duct to be determined continuously.

FIG. 3 is a diagram showing a second embodiment of apparatus of the invention.

As in the first embodiment, the multiphase fluid under pressure that flows in a duct 10 has a sample taken from a substantially vertical first length 12 of said duct via a sample-taking tube 18 under the control of first valve-forming means 24. The first length is also a substantially vertical length in which the fluid is agitated and flows upwards. Here again, the fluid can be agitated in said first length 12 in various different ways, and in particular by placing a first Venturi 14 immediately beneath the length 12.

At its opposite end, the sample-taking tube 18 opens out into the top portion of a separator receptacle 20 which may be implemented, in particular, in the manner described above with reference to FIG. 2.

The apparatus also includes a gaseous phase exhaust tube 22 connecting the top of the separator receptacle 20 to a second length 16 of the duct 10 via second valve-forming means 26. The second length 16 is placed downstream from the first length 12 and the pressure that obtains therein is lower than that which obtains in said first length. In the embodiment shown in FIG. 3, the second length 16 is constituted by a second Venturi.

This second embodiment differs from the first embodiment essentially in that the liquid phase exhaust tube 54 connects the bottom of the separator receptacle 20 to the second length 16 of the duct 10. In addition, a device 56 for measuring the volume ratio of the liquid phases is located in the tube 54. Instead of taking samples and measurements discontinuously as in the first-described embodiment, this second embodiment makes it possible to perform measurements continuously.

As before, use of the apparatus of FIG. 3 is preceded by a step during which the apparatus is pressurized and filled. During this step, gas under a pressure not less than that prevailing in the first length 12 of the duct is injected into the tubes 18, 22, and 54 in order to move all liquid from the apparatus and prevent any sudden drop in pressure occurring when sample-taking begins.

Thereafter, all three valve-forming means 24, 26, and 52 are opened simultaneously, thereby having the effect of continuously taking a fraction of the liquid flowing in the first length 12 of the duct 10 because of the difference in pressure that obtains between the length 16 and 12. This fluid fraction is conveyed by the tube 18 into the separator receptacle 20 where the liquid phases are separated by gravity from the gaseous phase. The gaseous phase is returned to the second length 16 of the duct via the tube 22 while the liquid phases are returned to the same length 16 by the tube 54. The flow rates are then adjusted, e.g. by acting on the valve-forming means 24, 26, and 52, so that the liquid-gas interface remains permanently situated within the separator receptacle 20. This situation can be monitored either visually as described above, or else by appropriate level-detection means. It is then certain that the fluid which flows into the device 56 is essentially constituted by an emulsion of the liquid phases L1 and L2 of the fluid flowing along the duct 10.

The device 56 is constituted by any known device making it possible to measure the volume ratio of the liquid phases L1 and L2. Thus, it may be constituted by an optical probe, by an optical apparatus that operates by photon absorption, by apparatus for measuring dielectric constants, by apparatus for measuring capacitance, by apparatus for measuring conductivity, by nuclear measurement apparatus, etc.

It should be observed that the device 56 is selected to make it possible to perform accurate measurement in the presence of a small quantity of gas phase in the fluid passing therethrough. A very small fraction by volume of gas phase may be entrained by the liquid phases or may be produced by the pressure drop to which the liquid phases are subjected on being entrained in the tube 54.

Compared with the first preferred embodiment, the apparatus described above with reference to FIG. 3 has the advantage of operating continuously and automatically. In addition, measurements can be performed by electronic systems so that it is no longer essential for a person to be present.

I claim:

1. A method of studying the properties of a multiphase fluid flowing along a duct with a fluid confining wall, said duct having a separated first and second lengths thereof within which prevail respectively a first and second pressure and containing at least two liquid phases and a gaseous phase, in volume ratio to be determined by a sensor device, comprising the following steps:

an extracted fluid fraction of fluid is extracted from the substantially vertical first length of the duct, within which the fluid is agitated and flows upwards, the fraction being taken by an orifice of a first tube oriented at a certain distance from the wall of said length; and the taken fluid fraction is transferred into a thermally-insulated separator receptacle, having a top portion and an end wall, the initial pressure within the separator receptacle being close to the first pressure prevailing in the first length, and the separator receptacle top portion is connected via a second tube to the second length of the duct located downstream from the first length and the pressure within the separator receptacle is slightly lower than that of the first length so that a fluid sample is obtained which preserves the volume ratio of the liquid phases, said fluid sample in said separator receptacle with a liquid-gas interface level and a liquid liquid interface level.

2. A method according to claim 1, in which all liquid is initially eliminated from the separator receptacle by filling said receptacle and the tubes which connect it to the duct with a gas at a pressure close to that which obtains in the first length.

3. A method according to claim 1, in which the volume ratio of the liquid phases is subsequently determined by isolating the separator receptacle from the duct and by measuring the levels of the liquid-gas and liquid-liquid interfaces in the separator receptacle.

4. A method according to claim 1, in which the density of an emulsion of the liquid phases is subsequently determined by isolating the separator receptacle from the duct, by weighing the separator receptacle before and after fluid fraction sample-taking, and by measuring the level of the liquid-gas interface in the separator receptacle.

5. A method according to claim 1, in which the separator receptacle is subsequently isolated from the duct, and then each of the liquid phases is successively withdrawn therefrom in order to study the properties of each liquid phase sequentially and separately.

6. A method according to claim 1, in which the volume ratio of the liquid phases is determined by continuously connecting the end wall of the separator receptacle to the second length of the duct via a device sensor for measuring said ratio.

7. A method according to claim 1, in which a cylindrical separator receptacle is used having a vertical axis and a uniform internal cross section.

8. A method according to claim 1, in which said fluid fraction is taken from the first length situated immediately above a first Venturi belonging to a flow rate measuring system.

9. A method according to claim 1, in which the top of the separator receptacle is connected to a second Venturi belonging to a flow rate measuring system and forming a second length of the duct.

10. A method according to claim 1, in which the fluid is a petroleum fluid containing water, liquid petroleum, and gaseous hydrocarbons.

11. Apparatus for studying the properties of a multiphase fluid flowing along a duct and containing at least two liquid phases and a gaseous phase, the apparatus comprising:

a sample-taking tube having a first end opening out into a substantially vertical first length of the duct within which the fluid is agitated and flows upwards, and which opens out within said length at a certain distance from the wall thereof;

a separator receptacle, with a heat insulating sheath, into which there opens out a second end of the sample-taking tube;

a tube for exhausting the gaseous phase, said tube connecting the separator receptacle to a second length of the duct, placed downstream from the first length, and at a slightly lower pressure than said first length;

valve-forming means placed in the sample-taking tube and in the tube for exhausting the gaseous phase and a tube for exhausting the liquid phase out of the separator receptacle.

12. Apparatus according to claim 12, further including means for measuring the levels of the liquid-gas and liquid-liquid interfaces in the separator receptacle.

13. Apparatus according to claim 12, in which a device for measuring the volume ratio of the liquid phases is located in the liquid phase exhaust tube connecting the bottom of the separator receptacle to the second length of the duct.

14. Apparatus according to claim 12, in which the separator receptacle comprises a transparent vertical tube surrounded by a metal outer sheath, with an observation window being formed through the sheath.

15. Apparatus according to claim 11, in which the separator receptacle is a cylindrical receptacle, having a vertical axis and an internal cross section that is substantially uniform.

16. Apparatus according to claim 12, in which the sample-taking tube opens out into the first length of the duct immediately above a first Venturi belonging to a flow rate measuring system.

17. Apparatus according to claim 12, in which the second length of the duct includes a second Venturi belonging to the system for measuring flow rate.

* * * * *